United States Patent
Prance et al.

(10) Patent No.: US 8,054,061 B2
(45) Date of Patent: Nov. 8, 2011

(54) ELECTRIC POTENTIAL SENSOR

(75) Inventors: Robert Prance, Brighton (GB); Christopher Harland, Brighton (GB)

(73) Assignee: University of Sussex (GB)

( * ) Notice: Subject to any disclaimer, the term of this patent is extended or adjusted under 35 U.S.C. 154(b) by 98 days.

(21) Appl. No.: 12/374,359

(22) PCT Filed: Jul. 13, 2007

(86) PCT No.: PCT/GB2007/002645
§ 371 (c)(1),
(2), (4) Date: Mar. 3, 2009

(87) PCT Pub. No.: WO2008/009906
PCT Pub. Date: Jan. 24, 2008

(65) Prior Publication Data
US 2009/0167324 A1 Jul. 2, 2009

(30) Foreign Application Priority Data
Jul. 18, 2006 (GB) .................................. 0614261.6

(51) Int. Cl.
*G01R 19/00* (2006.01)
*G01R 27/26* (2006.01)
(52) U.S. Cl. ................ 324/76.11; 324/686; 324/658
(58) Field of Classification Search ............. 324/76.11, 324/348, 72, 686, 661, 658, 754.28, 76.66, 324/519; 702/1, 57, 127
See application file for complete search history.

(56) References Cited

U.S. PATENT DOCUMENTS

| 3,404,341 A | 10/1968 | Young |
| 3,887,877 A | 6/1975 | Vosteen |
| 5,343,404 A * | 8/1994 | Girgis ............................ 702/72 |

FOREIGN PATENT DOCUMENTS

| GB | 2282501 A | 4/1995 |
| WO | 03048789 A2 | 5/2003 |

OTHER PUBLICATIONS

Prance et al., An Ultra-Low-Noise Electrical-Potential Probe for Human-Body Scanning, Mar. 1, 2000, Measurement Science and Technology, vol. 11, No. 3, pp. 291-297.*
Gebrial W et al: "Non destructive testing of materials using a novel electric potential sensor" Sensors Applications Symposium, 2006. Proceeding of the 2006 IEEE Houston, Texas, USA Feb. 7-9, 2006, Piscataway, NJ, USE, IEEE, Feb. 7, 2006, pp. 115-118.

* cited by examiner

*Primary Examiner* — Hoai-An D Nguyen
(74) *Attorney, Agent, or Firm* — Brooks Kushman P.C.

(57) ABSTRACT

The invention provides an electric potential sensor including, at least one detection electrode arranged for capacitive coupling with a sample under test and for generating a measurement signal, and a sensor amplifier adapted to receive the measurement signal as input and to supply an amplified detection signal as output. An input impedance enhancing element provides a high input impedance to the sensor amplifier for increasing the sensitivity of the electrode to reduced electric potentials, and a feedback element applies a coherent feedback signal to the input of the sensor amplifier for enhancing the signal to noise ratio of the sensor.

10 Claims, 3 Drawing Sheets

ELECTRIC POTENTIAL SENSOR

FIELD OF THE INVENTION

The present invention concerns electric potential sensors for use for the measurement of potentials in a variety of applications, including for example the fields of medical applications and microscope applications, such as microscopic imaging and spectrum analysis, as well as nuclear magnetic resonance (NMR) applications, such as NMR imaging and spectroscopy.

BACKGROUND TO THE INVENTION

In order to create a sensitive electrodynamic measuring device, it is customary to provide a high input impedance and thereby reduce the power of the input signal required to operate the device. However, electronic circuits with a very high input impedance tend to be unstable, and so practical devices are usually a compromise between achieving the necessary degree of sensitivity, providing the desired input impedance and ensuring an acceptable degree of stability.

In International Patent Application No. WO 03/048789, an electrodynamic sensor is disclosed in which a number of different circuit techniques are combined to achieve several orders of magnitude improvement in sensitivity, by comparison with previously known electrodynamic sensors, whilst still maintaining sufficient stability to permit a relatively unskilled operator to make measurements in everyday conditions. According to this earlier application, an electrodynamic sensor is provided comprising a high input impedance electrometer, which is adapted to measure small electrical potentials originating from an object under test and which employs at least one input probe having no direct electrical contact with the object. The circuit arrangement of the electrometer of this invention comprises an amplifier, which includes a combination of ancillary circuits providing feedback from the output of the amplifier and arranged cumulatively to increase the sensitivity of the electrometer to the small electrical potentials whilst not perturbing the electrical field associated therewith, the ancillary circuits serving to provide at least two of: guarding, bootstrapping, neutralisation, supply rail drift correction, supply modulation and offset correction for said sensor.

Whilst these features assist in providing a sensor with high input impedance and a relatively stable operation, nevertheless, in situations where there may be weak capacitive coupling to, or a signal of small amplitude generated by, a source or sample under test, noise problems may still remain and may inhibit or prevent accurate signal measurement. This is particularly the case in certain medical and microscopic applications in which there is only a weak capacitive coupling and yet highly accurate signal measurement is essential, for example in a remote off-body mode of sensing in which the or each probe has no physical contact with the human body and typically the weak capacitive coupling would be <1 pF.

More particularly, in applications where there is a weak coupling between a sample under test and the sensor electrode, the capacitive coupling to the sample may be comparable with or much smaller than the input capacitance of the sensor. In this case, the measurement signal received by the sensor is attenuated by the capacitive potential divider formed by the coupling capacitance and the input capacitance and may be difficult to capture.

Furthermore, the use of the output signal from the amplifier as the feedback signal has the disadvantage that such a signal is a broadband signal, which may have a poor signal to noise ratio. Hence, the noise is then fed back to the amplifier input with the feedback signal, causing further degradation of the signal to noise ratio.

There is thus a significant need for an electric potential sensor in which the possibility for accurate signal measurement is enhanced in cases of weak capacitive coupling to a sample under test.

Such a need is especially pronounced in cases where accuracy of signal measurement is critical.

There is also a significant need for an electric potential sensor in which the signal to noise ratio is substantially improved.

SUMMARY OF THE INVENTION

The present invention seeks to overcome the problems described above and to provide a novel electric potential sensor, which is capable of highly accurate signal measurement.

The present invention, at least in the preferred embodiments described below, also seeks to provide an electric potential sensor in which the signal to noise ratio is significantly enhanced.

The present invention further seeks to provide various techniques, and combinations of techniques, for enhancing the signal to noise ratio in an electric potential sensor.

More especially, at least in the preferred embodiments described below, the present invention seeks to provide various techniques for improvement of the signal to noise ratio in an electric potential sensor using a coherent narrowband feedback signal.

According to the present invention, there is provided an electric potential sensor comprising:
  at least one detection electrode arranged for capacitive coupling with a sample under test and for generating a measurement signal;
  a sensor amplifier adapted to receive the measurement signal as input and to supply an amplified detection signal as output;
  input impedance enhancing means for providing a high input impedance to the sensor amplifier for increasing the sensitivity of the electrode to reduced electric potentials; and
  feedback means for applying a coherent feedback signal to the input of the sensor amplifier for enhancing the signal to noise ratio of the sensor.

The present invention is thus concerned with improving the signal to noise ratio by applying a coherent feedback signal.

In contrast with the usual practice for electrodynamic sensors, the feedback signal is not a broadband signal derived directly from the output of the sensor but is a coherent signal made available for feedback, and this significantly improves the signal to noise ratio.

According to one possibility, the feedback signal comprises the simplest case of a single frequency and the feedback means are arranged such that the input impedance of the sensor is only enhanced at the exact frequency and phase of the feedback signal. In other words, the sensor is arranged differentially to amplify the measurement signal thus increasing the signal to noise ratio. In this case, the sensor becomes tuned to the feedback signal frequency, and rejects all other frequencies due to the lower sensitivity of the sensor in the absence of an effective feedback signal at other frequencies.

Advantageously, the coherent feedback signal may be used to provide bootstrapping, guarding and neutralisation, as desired.

The invention is particularly applicable in situations where a periodic signal is to be detected from a sample for generating a measurement signal for supply to the amplifier for amplification and output.

In one such embodiment of the invention, the electric potential sensor comprises an external source for providing a drive signal for exciting the sample being measured, and the coherent feedback signal is derived from this external source. The use of such an external source of excitation is a common situation in analysis applications, such as microscopic imaging of dielectric properties of materials. In this instance, the excitation signal from the external source of excitation may be suitably attenuated to provide a reference signal for use as the feedback signal.

In another such embodiment of the invention, the sample being measured may be self-exciting, in which case no external reference signal is available. An example of such a self-exciting sample might be an electronic circuit undergoing self-oscillation. In this case, a phase locked loop arrangement may be provided for deriving the coherent feedback signal from the output of the sensor amplifier. A considerable improvement in the overall signal to noise ratio is still possible in this instance, because of the restricted bandwidth in which the phase locked loop operates.

The invention is also applicable in situations where the sensor is designed to drive or excite a sample being measured for generating a measurement signal for supply to the amplifier for amplification and output, and where it is desirable to eliminate charging of the sample and maintain a minimum signal on the sample. An example of this would be in microscopic applications in which a large electric field could damage or destroy a small semi-conducting device, or the surface of a sample, being measured.

Such a sensor may be described as a zero voltage mode sensor, and the sensor in this instance advantageously comprises an external source for providing a drive signal for exciting the sample being measured, a feedback loop from the output of the sensor amplifier to the input, and a voltage summer arranged in the feedback loop so that both the feedback detection signal and the excitation signal from the external source of excitation are fed to the voltage summer for supply to the sample.

BRIEF DESCRIPTION OF THE DRAWINGS

The present invention will now be described further, by way of example, with reference to the accompanying drawings, in which.

DESCRIPTION OF PREFERRED EMBODIMENTS

Prior Art

Figure 1:
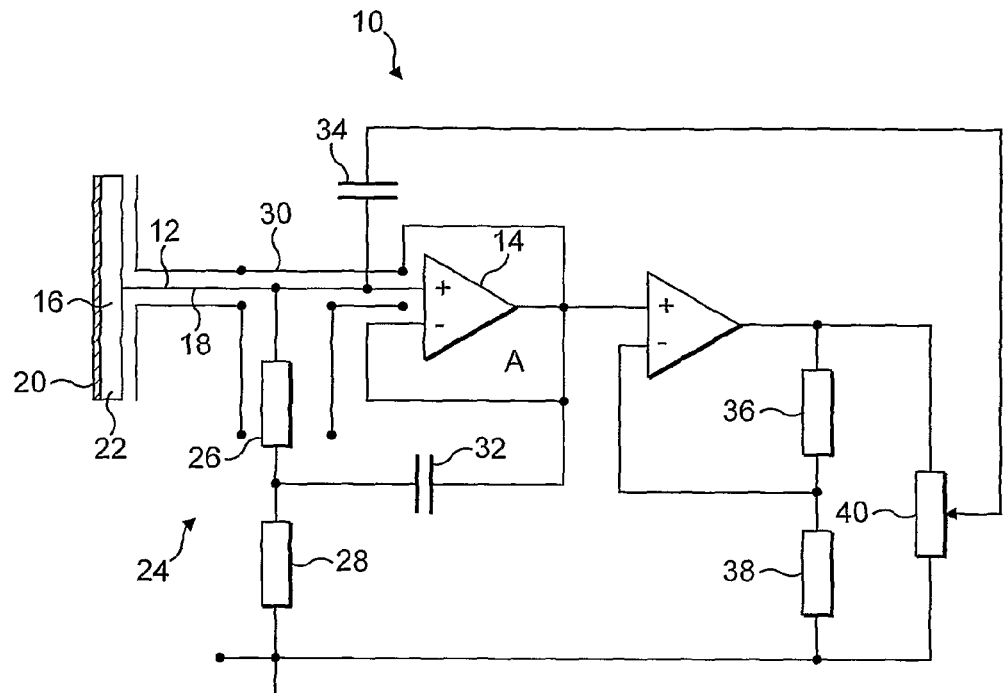
FIG. 1 is a circuit diagram of an electrodynamic sensor according to the prior art.

Referring to FIG. 1, an electrodynamic sensor as disclosed in International Patent Application No. WO 03/048789 will first be described.

As shown in FIG. 1, an eletrodynamic sensor 10 according International Patent Application number WO 03/048789 comprises a detection electrode 12 connected to the non-inverting input of a sensor amplifier 14. In use, the detection electrode 12 supplies a measurement signal as input to the sensor amplifier 14, which supplies an amplified detection signal as output.

The detection electrode 12 includes an electrode disc 16 mounted on a conductive stem 18, the electrode disc 16 comprising a surface oxide layer 20 on a substrate 22. The sensor amplifier 14 has a fixed input resistance 24, provided by two resistors 26, 28, connected between the electrode 12 and the non-inverting input of the amplifier 14, to provide a steady input bias current to the amplifier 14. In practice, the input resistor 24 will generally have a high resistance of the order of 100 GΩ or greater. The sensor amplifier 14 also has a guard 30 physically surrounding the input circuitry including the electrode 12 and the resistor 26 and providing a shield driven by the output of the amplifier 14. Stray capacitance is thus alleviated by means of this positive feedback technique by maintaining the same potential on the guard or shield 30 as on the input detection electrode 12.

In addition to the guard 30, further circuit components are provided for bootstrapping, comprising a capacitor 32 arranged to apply the output voltage of the amplifier 14 to the mid point of the resistance 24, which occurs between the two resistors 26, 28, as well as for neutralisation, comprising another feedback arrangement including a capacitor 34 connected to the non-inverting terminal of the amplifier 14. Additional resistors 36, 38 and a potentiometer 40 are provided to set the neutralisation to a desired level, as described in International Patent Application number WO 03/048789.

Driven Neutralisation—Reference Source

Figure 2:
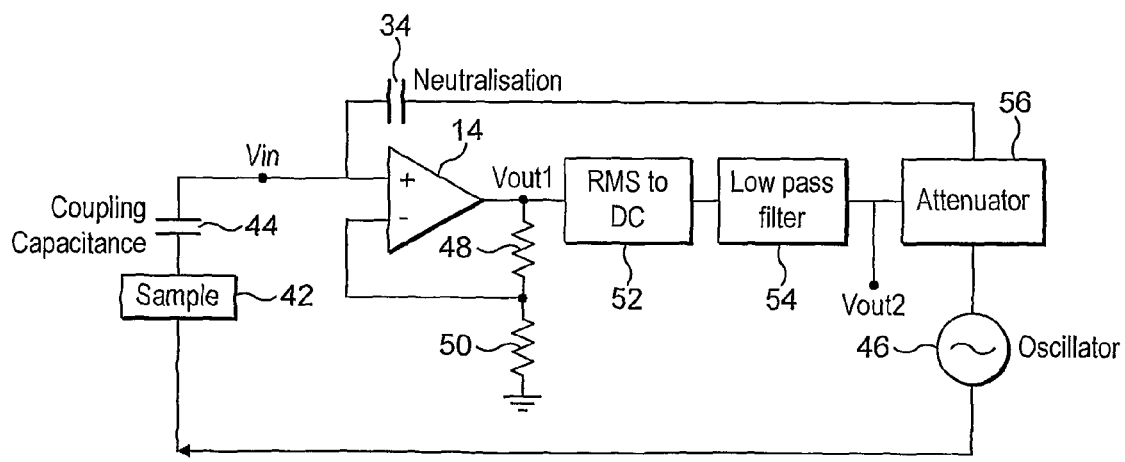
FIGS. 2 and 2a are block diagrams of a first embodiment of electrodynamic sensor according to the present invention, employing neutralisation, and a modification thereof.

Referring now to FIG. 2, a first embodiment of the invention will be described. Although neutralisation may be used to increase dramatically the input impedance of the electrodynamic sensor of FIG. 1, as described in International Patent Application number WO 03/048789, the signal to noise ratio is not enhanced by this technique since the noise present at the sensor output is fed back to the sensor input.

In many situations where neutralisation is important, for example in microscope applications, the sample is excited by an externally applied signal. In these cases, a reference signal is available from the oscillator providing the drive signal for the sample, and this reference may be used to provide a neutralisation signal for the sensor as shown in FIG. 2.

The electrodynamic sensor of FIG. 2 includes some of the same elements as the FIG. 1 sensor. Accordingly, like parts are designated by the same reference numerals and will not be described further. As shown, the detection electrode 12 of the sensor is represented by the input $V_{in}$ and is coupled to a sample 42 being measured by way of a capacitor 44 representing the coupling capacitance to the sample. The sample is driven or excited by a reference oscillator 46, and hence an AC measurement signal is produced at the sensor input $V_{in}$, which is connected to the non-inverting input of the operational amplifier 14. As a result, the amplifier 14 supplies an amplified AC detection signal at its output $V_{out1}$. The output $V_{out1}$ is connected by way of resistors 48, 50 to ground and by way of a root mean square (RMS) converter circuit 52 and a low pass filter 54 to an attenuator 56, from which a reference signal $V_n$ is taken for feedback. These circuits serve for level control of the reference signal $V_n$ which is fed back by way of capacitor 34 to the non-inverting input of the amplifier 14 to provide neutralisation. The gain of this positive feedback loop may be so controlled such that maximum neutralisation is achieved within the limit of stable operation.

The embodiment of FIG. 2 thus includes an automatic gain control (AGC) feedback loop to control the amplitude of the neutralisation signal $V_n$ in order to prevent oscillation, with the amplitude of the feedback signal being controlled by the amplitude of the sensor output signal at a control output $V_{out2}$. The feedback loop here includes the RMS converter circuit 52, the low pass filter 54 and the attenuator 56. The control output of the sensor $V_{out2}$ is taken from the AGC feedback line between the low pass filter 54 and the attenuator 56 and, since the reference and measurement signal frequencies are the same, the AGC control voltage $V_{out2}$ will be a quasi-DC control signal providing information about the sample 42 derived from the amplitude of the AC measurement signal supplied to the amplifier 14.

This arrangement has the effect of enhancing significantly the input impedance of the sensor, but only at the frequency of the applied signal and only for components of constant phase, hence providing an improved signal to noise ratio.

Figure 2A:
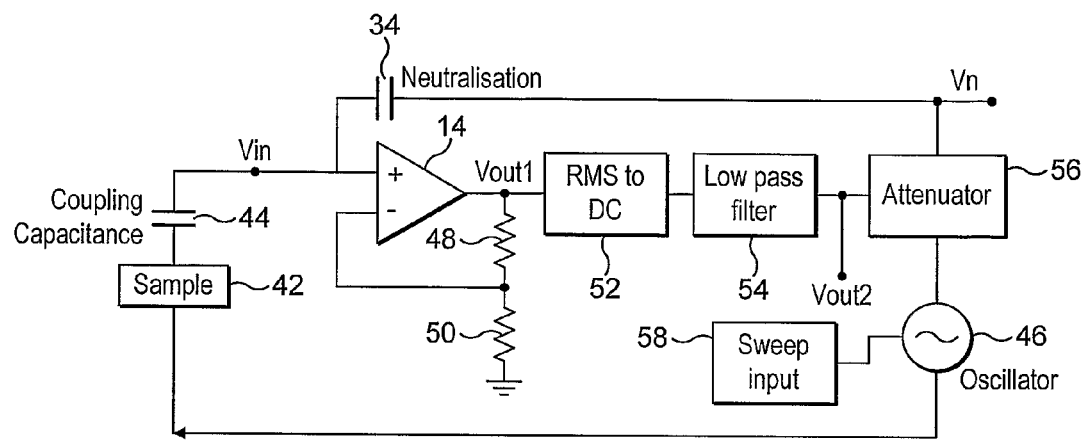

An extension of the technique described with reference to FIG. 2 allows the frequency of the reference oscillator 46 to be swept under the control of a sweep control arrangement 58 shown in FIG. 2a. In practice, the sweep control arrangement 58 for sweeping the frequency of the oscillator may be either a digital control circuit connected to the oscillator 46 (as shown) for controlling the frequency digitally via a suitable interface or an arrangement (not shown) for frequency modulating the source via an appropriate FM input or a circuit (not shown) using an analogue quasi-DC level derived independently to set the operating frequency via a swept input. As already stated, since the reference and signal frequencies are the same, the AGC control voltage at the control output $V_{out2}$ will be a quasi-DC signal. This will vary with the amplitude of the measured signal and as a function of the frequency, and so may be used to provide a spectral plot as the frequency of the reference oscillator is swept. This arrangement resembles a spectrum analyser in operation.

Fully Driven Sensor—Reference Source

Figure 3:
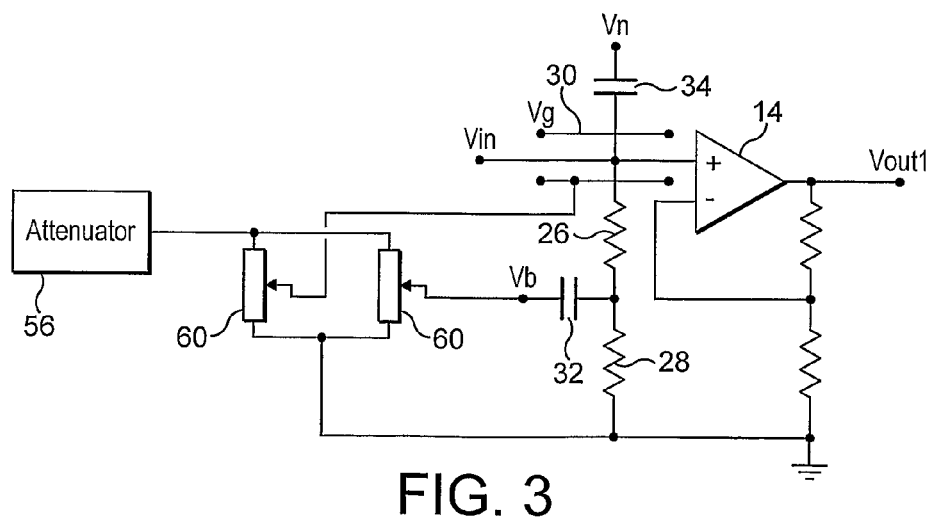
FIG. 3 is a circuit diagram of a modification to a detail of the FIG. 2 circuit, employing guarding and bootstrapping in addition to neutralisation.

The embodiment of FIG. 2, in which the external reference source 46 is used to provide a neutralisation signal $V_n$, may be extended also to provide signals $V_g$, $V_b$, suitable respectively for guarding and bootstrapping, with commensurate additional improvements in the signal to noise ratio. This variation is shown in FIG. 3, in which the reference signal from the oscillator 46 and attenuator 56 is fed back as a guard signal $V_g$ to the shield or guard 30 surrounding the electrode 12. In addition, the reference signal is fed back by way of the capacitor 32 and two resistors 26, 28 to the non-inverting input of the amplifier 14 as a bootstrapping signal $V_b$. The individual relative signal levels required for each feedback technique are obtained from a set of independent potential dividers 60, as shown in FIG. 3, driven by the external reference source or oscillator 46. The overall level of the feedback signals is set globally based on the amplitude of the output signal $V_{out2}$ through the use of the AGC loop as described in relation to FIG. 2.

Driven Neutralisation—No Reference

Figure 4:
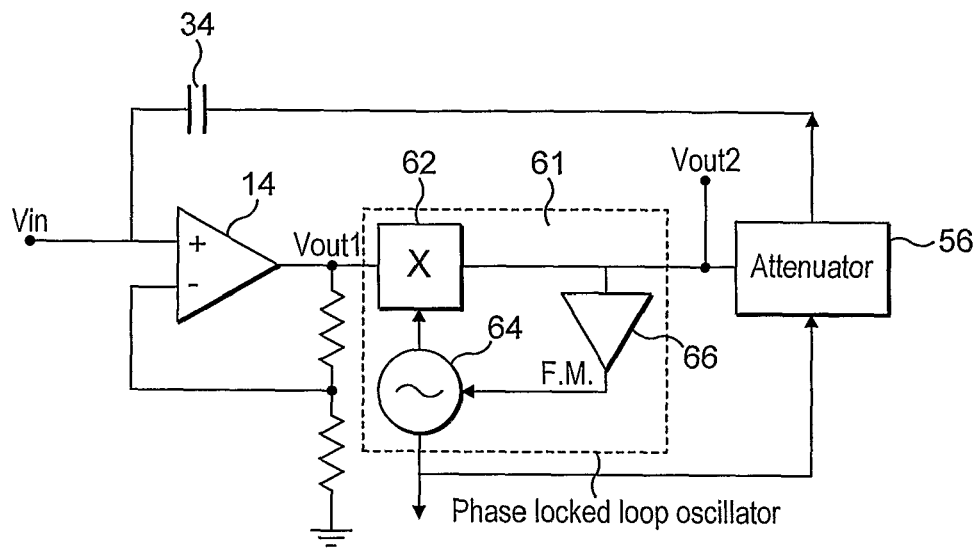
FIG. 4 is a block diagram of a second embodiment of electrodynamic sensor according to the present invention, employing neutralisation and a phase locked loop.

Another variation on the embodiment of FIGS. 2 and 3 employs a phase lock loop oscillator to derive the drive and neutralisation signals, as shown in FIG. 4. In this case, the sample is self-exciting, and thus the drive oscillator 46 is not present and the local reference signal from the drive oscillator 46 is not available. However, an enhanced signal to noise ratio may still be achieved by the introduction of an oscillator into the sensor which is phase locked to the detection signal output by the amplifier 14.

The embodiment of FIG. 4 comprises a phase locked loop oscillator 61 which is connected to the output $V_{out1}$ of the amplifier 14 and which comprises a frequency multiplier 62 arranged to receive the signal $V_{out1}$ and an output signal from an oscillator 64. An amplifier 66 feeds back the output from the frequency multiplier 62 to the oscillator 64 in order to frequency modulate the signal output by the oscillator 64. As a result, the amplified detection signal is mixed with the output from the oscillator 64 to form the phase locked loop.

In operation, the oscillator 64 sweeps in frequency until a beat is found with the measurement signal, at which point the sweep will be frozen. Because there is no constant phase relationship between the sample and the oscillator 64, the beat will take the form of a low frequency waveform, which will become DC when the phase lock is achieved. This DC signal is output as the overall output $V_{out2}$ of the sensor and is also used as an AGC signal whose amplitude controls the amplitude of the feedback signal used for neutralisation. For this purpose, the DC signal is fed back by way of the attenuator 56 and the capacitor 34 to the non-inverting input of the amplifier 14 to provide the neutralisation signal. In use, the phase locked loop oscillator 61 will sweep in operation until a measurement signal is acquired and will then feed back a phase locked signal to enhance the input impedance of the sensor at this frequency only. This serves to increase the input impedance at the signal frequency without broadband noise being fed back to the amplifier input.

In a first variation of the FIG. 4 embodiment, guarding and bootstrap signals may also be derived from the output of the phase locked loop oscillator 61, using similar circuit features to those shown in FIG. 3, with a commensurate improvement in the signal to noise ratio.

In a further variation of the FIG. 4 embodiment, the oscillator 64 may in addition supply a drive output for exciting the sample, as in the case of the FIG. 2 embodiment.

Zero Voltage Mode Sensor

Figure 5:
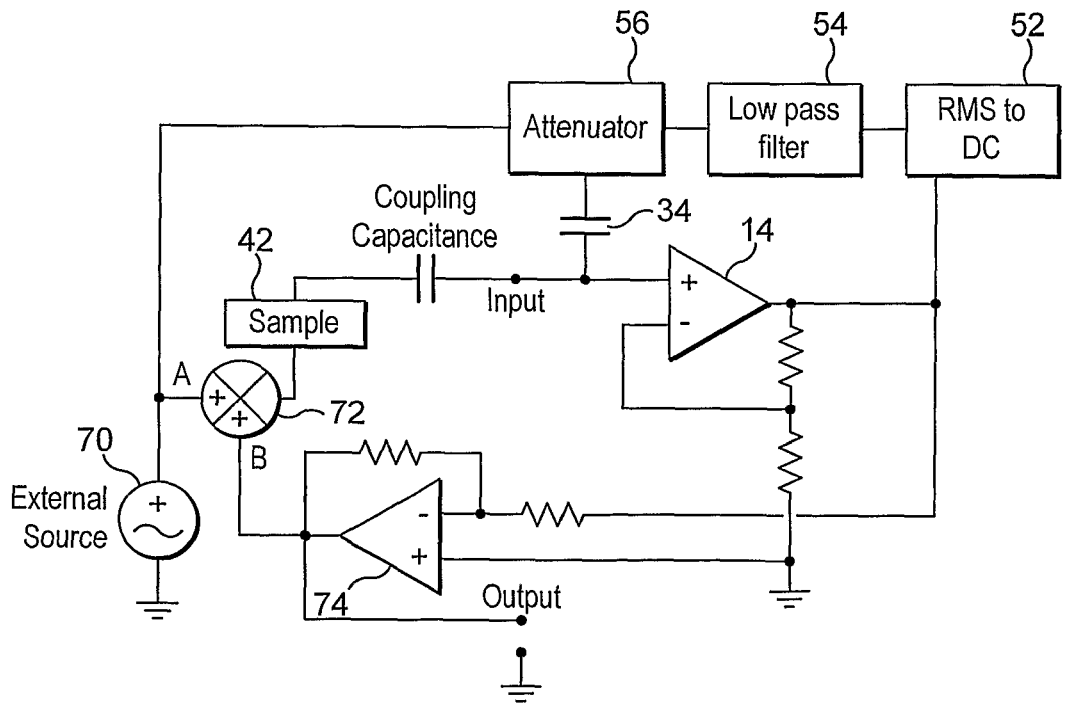
FIG. 5 is a circuit diagram of a third embodiment of electrodynamic sensor according to the present invention, comprising a zero voltage mode sensor.

Turning now to FIG. 5, a further embodiment of the invention will be described for use in the cases where for example charging of the sample needs to be eliminated. One example of this is where problems caused by relative motion of the sample and the sensor need to be minimised. Another important example is in microscopic applications where a large electric field may damage the surface of the sample. Again, this embodiment employs some of the same circuit features as the previous embodiments and like parts will be designated by the same reference numerals and will not be described further.

According to this embodiment, the sample 42 is excited by an oscillator 70 by way of a voltage summer 72, which also receives the detection signal fed back from the output $V_{out1}$ of the amplifier 14. By closing the feedback loop with the voltage summer 72, it is possible to ensure that only a small error signal appears on the sample 42. The detection signal at the output $V_{out1}$ is fed back to the voltage summer 72 by way of a further amplifier 74, which is used to set the loop gain and time constant for optimum operation. The signal to noise is thus enhanced by removing artefacts which may be caused by the presence of large signals on the sample.

In this embodiment, the oscillator 70 is again used to provide a reference signal for feedback, as shown in FIG. 2. For simplicity, only the features required for neutralisation have been shown in FIG. 5 but, of course, guarding and bootstrapping may also be employed as described with reference to FIG. 3. In all these cases, the guarding, bootstrapping and neutralisation signals are derived from the coherent source 70, and this enhances the signal to noise ratio as described previously.

Use of the FIG. 5 embodiment is restricted to the case where the sample 42 is excited with an external signal.

The invention claimed is:

1. An electric potential sensor, comprising:
   at least one detection electrode arranged for capacitive coupling with a sample under test and for generating a measurement signal, the at least one detection electrode being arranged to generate an AC measurement signal;
   a sensor amplifier adapted to receive the measurement signal as input and to supply an amplified detection signal as output;
   input impedance enhancing means for providing a high input impedance to the sensor amplifier for increasing the sensitivity of the electrode to reduced electric potentials;
   an oscillator arranged for generating an oscillator output having a frequency corresponding with the frequency of the measurement signal; and
   feedback means responsive to the oscillator output for producing a feedback reference signal for applying a coherent feedback to the input of the sensor amplifier for enhancing the signal to noise ratio of the sensor.

2. A sensor according to claim 1 in which the input enhancing means is arranged to employ the reference feedback signal to provide at least one of bootstrapping, guarding and neutralisation.

3. A sensor according to claim 1 further comprising means for providing a control output from the sensor amplifier for controlling the level of the feedback reference signal.

4. A sensor according to claim 1 in which the feedback reference signal comprises a single frequency and in which the feedback means cooperate with the input impedance enhancing means such that the input impedance of the sensor is enhanced at the frequency and phase of the feedback reference signal.

5. A sensor according to claim 1 in which the sensor amplifier is arranged differentially to amplify the measurement signal in order to increase the signal to noise ratio at a selected signal frequency band.

6. A sensor according to claim 1 in which the oscillator comprises an external source for providing a drive signal for exciting the sample being measured.

7. A sensor according to claim 6 further comprising an attenuator for attenuating the drive signal from the external source of excitation to provide the feedback reference signal.

8. A sensor according to claim 1 in which the oscillator comprises a phase locked loop oscillator for deriving the feedback reference signal from the output of the sensor amplifier.

9. A sensor according to claim 1 further comprising an oscillator circuit which is arranged to generate an oscillator output that sweeps in frequency, for deriving a signal of varying frequency from the output of the sensor amplifier for providing the feedback reference signal.

10. A sensor according to claim 1 in which the oscillator comprises an external source for providing a drive signal for exciting the sample being measured, a feedback loop from the output of the sensor amplifier to the input, and a voltage summer arranged in the feedback loop so that both the feedback reference signal and the excitation signal from the external source of excitation are fed to the summer for supply to the sample.

* * * * *